US 11,612,403 B2

(12) United States Patent
Kabala et al.

(10) Patent No.: US 11,612,403 B2
(45) Date of Patent: Mar. 28, 2023

(54) MULTI-FUNCTION SURGICAL TRANSECTION INSTRUMENT

(71) Applicant: COVIDIEN LP, Mansfield, MA (US)

(72) Inventors: Rachael L. Kabala, Fort Collins, CO (US); James D. Allen, IV, Broomfield, CO (US); Thomas E. Drochner, Longmont, CO (US); John A. Hammerland, III, Arvada, CO (US); Daniel A. Joseph, Golden, CO (US)

(73) Assignee: Covidien LP, Mansfield, MA (US)

( * ) Notice: Subject to any disclaimer, the term of this patent is extended or adjusted under 35 U.S.C. 154(b) by 774 days.

(21) Appl. No.: 16/580,384

(22) Filed: Sep. 24, 2019

(65) Prior Publication Data

US 2020/0107845 A1 Apr. 9, 2020

Related U.S. Application Data

(60) Provisional application No. 62/740,598, filed on Oct. 3, 2018.

(51) Int. Cl.
*A61B 17/22* (2006.01)
*A61B 17/072* (2006.01)

(52) U.S. Cl.
CPC .. *A61B 17/22031* (2013.01); *A61B 17/07207* (2013.01); *A61B 2017/07271* (2013.01); *A61B 2017/07285* (2013.01)

(58) Field of Classification Search
CPC ........ A61B 17/22031; A61B 17/07207; A61B 2017/07271; A61B 2017/07285;
(Continued)

(56) References Cited

U.S. PATENT DOCUMENTS

D249,549 S   9/1978 Pike
D263,020 S   2/1982 Rau, III
(Continued)

FOREIGN PATENT DOCUMENTS

CN   201299462 Y   9/2009
DE   2415263 A1   10/1975
(Continued)

OTHER PUBLICATIONS

Heniford et al. "Initial Research and Clinical Results with an Electrothermal Bipolar Vessel Sealer" Oct. 1999.
(Continued)

*Primary Examiner* — Brooke Labranche
(74) *Attorney, Agent, or Firm* — Carter, DeLuca & Farrell LLP

(57) ABSTRACT

A surgical instrument includes a housing having a first handle and an elongated shaft extending therefrom. An end effector is disposed at a distal end of the elongated shaft and includes first and second jaw members, the first jaw member including a staple cartridge configured to house a series of staples therein. A second handle is operably coupled to the housing and is selectively moveable relative to the first handle to actuate the first and second jaw members between an open position and a closed position for grasping tissue. A first switch is activatable to supply energy to one of the jaw members. A stapler mode switch is actuatable between an unactuated position wherein movement of the second handle moves the jaws to the second position and an actuated position wherein movement of the second handle moves the jaws to the second position and drives the staples through tissue.

20 Claims, 6 Drawing Sheets

(58) Field of Classification Search
CPC ........... A61B 2017/00367; A61B 2018/00172;
A61B 2018/00297; A61B 2018/00589;
A61B 2018/0063; A61B 2018/0091;
A61B 2018/00916; A61B 2018/00958;
A61B 2018/1452; A61B 2218/002; A61B
2218/007; A61B 18/1445; A61B
2090/0807

See application file for complete search history.

(56) References Cited

U.S. PATENT DOCUMENTS

| | | | |
|---|---|---|---|
| D295,893 | S | 5/1988 | Sharkany et al. |
| D295,894 | S | 5/1988 | Sharkany et al. |
| D298,353 | S | 11/1988 | Manno |
| D299,413 | S | 1/1989 | DeCarolis |
| D343,453 | S | 1/1994 | Noda |
| D348,930 | S | 7/1994 | Olson |
| D349,341 | S | 8/1994 | Lichtman et al. |
| D354,564 | S | 1/1995 | Medema |
| 5,403,312 | A * | 4/1995 | Yates ............... A61B 17/07207 606/49 |
| D358,887 | S | 5/1995 | Feinberg |
| D384,413 | S | 9/1997 | Zlock et al. |
| H1745 | H | 8/1998 | Paraschac |
| D402,028 | S | 12/1998 | Grimm et al. |
| D408,018 | S | 4/1999 | McNaughton |
| D416,089 | S | 11/1999 | Barton et al. |
| D424,694 | S | 5/2000 | Tetzlaff et al. |
| D425,201 | S | 5/2000 | Tetzlaff et al. |
| H1904 | H | 10/2000 | Yates et al. |
| D449,886 | S | 10/2001 | Tetzlaff et al. |
| D453,923 | S | 2/2002 | Olson |
| D454,951 | S | 3/2002 | Bon |
| D457,958 | S | 5/2002 | Dycus et al. |
| D457,959 | S | 5/2002 | Tetzlaff et al. |
| H2037 | H | 7/2002 | Yates et al. |
| D465,281 | S | 11/2002 | Lang |
| D466,209 | S | 11/2002 | Bon |
| D493,888 | S | 8/2004 | Reschke |
| D496,997 | S | 10/2004 | Dycus et al. |
| D499,181 | S | 11/2004 | Dycus et al. |
| D502,994 | S | 3/2005 | Blake, III |
| D509,297 | S | 9/2005 | Wells |
| D525,361 | S | 7/2006 | Hushka |
| D531,311 | S | 10/2006 | Guerra et al. |
| D533,274 | S | 12/2006 | Visconti et al. |
| D533,942 | S | 12/2006 | Kerr et al. |
| D535,027 | S | 1/2007 | James et al. |
| D538,932 | S | 3/2007 | Malik |
| D541,418 | S | 4/2007 | Schechter et al. |
| D541,611 | S | 5/2007 | Aglassinger |
| D541,938 | S | 5/2007 | Kerr et al. |
| D545,432 | S | 6/2007 | Watanabe |
| D547,154 | S | 7/2007 | Lee |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| D582,038 | S | 12/2008 | Swoyer et al. |
| D617,900 | S | 6/2010 | Kingsley et al. |
| D617,901 | S | 6/2010 | Unger et al. |
| D617,902 | S | 6/2010 | Twomey et al. |
| D617,903 | S | 6/2010 | Unger et al. |
| D618,798 | S | 6/2010 | Olson et al. |
| D621,503 | S | 8/2010 | Otten et al. |
| D627,462 | S | 11/2010 | Kingsley |
| D628,289 | S | 11/2010 | Romero |
| D628,290 | S | 11/2010 | Romero |
| D630,324 | S | 1/2011 | Reschke |
| D649,249 | S | 11/2011 | Guerra |
| D649,643 | S | 11/2011 | Allen, IV et al. |
| D661,394 | S | 6/2012 | Romero et al. |
| D670,808 | S | 11/2012 | Moua et al. |
| D680,220 | S | 4/2013 | Rachlin |
| 9,084,608 | B2 | 7/2015 | Larson et al. |
| 9,211,657 | B2 | 12/2015 | Ackley et al. |
| 2012/0012638 | A1* | 1/2012 | Huang ................. A61B 17/1114 227/176.1 |
| 2014/0221995 | A1 | 8/2014 | Guerra et al. |
| 2014/0221999 | A1 | 8/2014 | Cunningham et al. |
| 2014/0228842 | A1 | 8/2014 | Dycus et al. |
| 2014/0230243 | A1 | 8/2014 | Roy et al. |
| 2014/0236149 | A1 | 8/2014 | Kharin et al. |
| 2014/0243811 | A1 | 8/2014 | Reschke et al. |
| 2014/0243824 | A1 | 8/2014 | Gilbert |
| 2014/0249528 | A1 | 9/2014 | Hixson et al. |
| 2014/0250686 | A1 | 9/2014 | Hempstead et al. |
| 2014/0257274 | A1 | 9/2014 | Mccullough, Jr. et al. |
| 2014/0257283 | A1 | 9/2014 | Johnson et al. |
| 2014/0257284 | A1 | 9/2014 | Artale |
| 2014/0257285 | A1 | 9/2014 | Moua |
| 2014/0276803 | A1 | 9/2014 | Hart |
| 2014/0284313 | A1 | 9/2014 | Allen, IV et al. |
| 2014/0288549 | A1 | 9/2014 | Mckenna et al. |
| 2014/0288553 | A1 | 9/2014 | Johnson et al. |
| 2014/0330308 | A1 | 11/2014 | Hart et al. |
| 2014/0336635 | A1 | 11/2014 | Hart et al. |
| 2014/0353188 | A1 | 12/2014 | Reschke et al. |
| 2015/0018816 | A1 | 1/2015 | Latimer |
| 2015/0025528 | A1 | 1/2015 | Arts |
| 2015/0032106 | A1 | 1/2015 | Rachlin |
| 2015/0051598 | A1 | 2/2015 | Orszulak et al. |
| 2015/0051640 | A1 | 2/2015 | Twomey et al. |
| 2015/0066026 | A1 | 3/2015 | Hart et al. |
| 2015/0080880 | A1 | 3/2015 | Sartor et al. |
| 2015/0080889 | A1 | 3/2015 | Cunningham et al. |
| 2015/0082928 | A1 | 3/2015 | Kappus et al. |
| 2015/0088122 | A1 | 3/2015 | Jensen |
| 2015/0088126 | A1 | 3/2015 | Duffin et al. |
| 2015/0088128 | A1 | 3/2015 | Couture |
| 2015/0094714 | A1 | 4/2015 | Lee et al. |
| 2016/0374978 | A1* | 12/2016 | Raad ....................... A61L 31/16 206/232 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 3/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A2 | 3/2003 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 | 2/1993 |
| JP | 6121797 A | 5/1994 |
| JP | 6285078 A | 10/1994 |
| JP | 6511401 | 12/1994 |
| JP | H06343644 A | 12/1994 |

(56) References Cited

FOREIGN PATENT DOCUMENTS

| | | | |
|---|---|---|---|
| JP | H07265328 A | 10/1995 |
| JP | 08056955 | 3/1996 |
| JP | 08252263 A | 10/1996 |
| JP | 8289895 A | 11/1996 |
| JP | 8317934 A | 12/1996 |
| JP | 8317936 A | 12/1996 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | H0630945 B2 | 11/2016 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 | 6/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surger" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C . . . (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremeich, abandoned.
U.S. Appl. No. 14/065,644, filed Oct. 29, 2013; inventor: Reschke, abandoned.

\* cited by examiner

MULTI-FUNCTION SURGICAL TRANSECTION INSTRUMENT

CROSS REFERENCE TO RELATED APPLICATION

The present application claims the benefit of and priority to U.S. Provisional Application Ser. No. 62/740,598, filed on Oct. 3, 2018 the entire contents of which are incorporated herein by reference.

BACKGROUND

Technical Field

The present disclosure relates generally to the field of surgical instruments. In particular, the disclosure relates to a multi-function surgical transection instrument for use with hepatic-related surgical procedures.

Background of Related Art

Surgical instruments such as electrosurgical forceps are commonly used in open and endoscopic surgical procedures to treat tissue, e.g., coagulate, cauterize, cut and/or seal tissue. The combination of mechanical clamping force and electrosurgical energy has been demonstrated to facilitate treating tissue and, specifically, sealing tissue. With respect to mechanical clamping pressure for tissue sealing, for example, it has been found that pressures within the range of about 3 kg/cm$^2$ to about 16 kg/cm$^2$ help ensure formation of effective and consistent tissue seals. Other pressures within or outside this range may be utilized for treating tissue in a different manner and/or for other purposes.

Electrosurgical forceps typically include a pair of jaw members that can be manipulated to grasp targeted tissue. More specifically, the jaw members may be approximated to apply a mechanical clamping force to the tissue, and are associated with at least one electrode to permit the delivery of electrosurgical energy to the tissue. The jaw members may be used in conjunction with a knife or an electrical cutting mechanism for cutting or transecting tissue.

During complicated surgical procedures, e.g., hepatic transection or resection, additional surgical instruments may need to be used along with a surgical forceps to supplement or replace specific functions of the forceps, e.g., ultrasonic instruments, sutures, clip appliers, staplers, coagulators, etc.

Various surgical techniques have been used in the past to facilitate liver transection, so-called "clamp crushing" and the use of intraoperative ultrasound being the most prominent. In these procedures, liver parenchyma is "crushed" out of the way leaving vessels and bile ducts exposed which can then be sealed with energy, clipped, stapled, cut or treated with monopolar or bipolar energy, cold knife, etc. More recently, technological advances have led to the development of new instruments for use with liver transections, e.g., Ligasure®, TissueLink, and Aquamantys™ for example. Moreover, advances in operative techniques have also contributed to a reduction in blood loss during liver transection. These include better delineation of the transection plane with the use of intraoperative ultrasound, and better inflow and outflow control of fluids.

Typically, a combination of instruments are utilized to perform a liver transection, e.g., such as one instrument that can employ clamp crushing and another that can deliver energy, to improve the safety of liver transection. Many of these instruments utilize various types of energy modalities to coagulate tissue, seal vessels, cut and transect hepatic tissue. Other instruments use different technology to treat tissue, e.g., the liver parenchyma tissue may be fragmented with ultrasonic energy and aspirated, thus exposing vascular and ductal structures that can be ligated or clipped with titanium hemoclips.

Ligasure® (Valley Lab, Tyco Healthcare (now Medtronic, Inc.), Boulder, Colo., USA) vessel sealing instruments are another line of instrumentation designed to seal small vessels using a different principle. By a combination of compression pressure and bipolar radiofrequency (RF) energy, the various instruments apply pressure and energy to denature the proteins in the collagen and elastin and allow them to fuse together the opposing layer of denatured proteins. These instruments are effective in sealing small vessels up to 7 mm in diameter. Ligasure® in combination with a clamp crushing technique has resulted in lower blood loss and faster transection speed in minor hepatic resections compared with conventional techniques of electrical cautery or ligature for controlling vessels in the transection plane.

RF ablation (RFA) is a relatively newer technique for liver transection. A Cool-tip® RF electrode (sold by Medtronic, Inc.) is inserted along the transection plane and RF energy is applied to create overlapping cylinders of coagulated tissue, followed by transection of the coagulated liver using a simple scalpel. This device and technique has the advantage of simplicity compared with the aforementioned transection devices and techniques but additional instruments may still need to be introduced to treat certain types of parenchymal tissue.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein. As used herein the term "tissue" is meant to include variously-sized vessels.

Provided in accordance with aspects of the present disclosure is a surgical instrument including a housing having a first handle depending therefrom and an elongated shaft extending distally from the housing. An end effector is disposed at a distal end of the elongated shaft and includes first and second jaw members each having an electrically conductive plate disposed thereon. The respective electrically conductive plates of the first and second jaw members are disposed in vertical opposition relative to one another. The first jaw member includes a staple cartridge configured to house a series of staples therein. A second handle is operably coupled to the housing and is selectively moveable relative to the first handle to actuate the first and second jaw members between a first position wherein the first and second jaw members of the end effector assembly are disposed in a spaced apart configuration relative to one another and second position wherein the jaw members cooperate to grasp tissue disposed therebetween.

A first switch is disposed on the housing and is activatable to supply electrical energy from an electrical energy source to at least one of the electrically conductive plates of the first or second jaw members. A stapler mode activation mechanism is operably coupled to the second handle and is actuatable between a first, unactuated position, wherein movement of the second handle towards the first handle moves the jaw members to the second position and a second, actuated, position wherein movement of the second handle towards the first handle moves the jaw members to the second position and drives the staples through tissue disposed between the jaw members.

In aspects according to the present disclosure, the second jaw member includes a corresponding series of pockets defined therein disposed in registration with the series of staples disposed in the first jaw member. In other aspects according to the present disclosure, the first switch, when activated, provides electrical energy to the respective at least one jaw member to coagulate tissue.

In yet other aspects according to the present disclosure, a second switch is disposed on an inner facing surface of the first handle in alignment with the second handle such that actuation of the second handle activates the second switch during movement thereof. The second switch is operably connected to both electrically conductive plates of the first and second jaw members and is configured to supply electrical energy from an electrical energy source to tissue disposed between the electrically conductive plates. In aspects according to the present disclosure, the second switch is configured to supply electrical energy to seal tissue disposed between the electrically conductive plates of the first and second jaw members.

In other aspects according to the present disclosure, at least one of the jaw members includes at least one stop member disposed thereon configured to regulate a gap between electrically conductive plates when the jaw members are disposed in the second position.

In still other aspects according to the present disclosure, a trigger assembly is operably associated with the housing and includes a trigger configured to selectively advance a knife between the first and second jaw members upon actuation thereof. In aspects according to the present disclosure, the knife is advanceable via actuation of the trigger between a first position wherein the knife is disposed proximal the first and second electrically conductive plates of the first and second jaw members to a second position wherein the knife translates through respective channels defined within the first and second electrically conductive plates of the first and second jaw members.

In yet other aspects according to the present disclosure, a rotation knob is operably associated with the elongated shaft of the housing and is selectively rotatable relative to the housing to rotate the elongated shaft and the end effector at the distal end thereof. In still other aspects according to the present disclosure, the second switch is configured to include tactile feedback or an audible tone to advise the user prior to activation of electrical energy.

In aspects according to the present disclosure, a release mechanism is disposed on the housing and is operably associated with the end effector. The release mechanism is actuatable to uncouple the end effector from a distal end of the elongated shaft. In other aspects according to the present disclosure, the release mechanism is actuatable to couple and uncouple the end effector from the distal end of the shaft. In still other aspects according to the present disclosure, the release mechanism cooperates with a coupler disposed within the elongated shaft to uncouple the end effector from the shaft.

In accordance with other aspects of the present disclosure is a surgical instrument that includes a housing having a first handle depending therefrom and an elongated shaft that extends distally from the housing. An end effector is disposed at a distal end of the elongated shaft and includes first and second jaw members each having an electrically conductive plate disposed thereon. The first jaw member includes a staple cartridge configured to house a series of staples therein and the second jaw member includes a series of corresponding pockets defined therein in vertical registration with the series of staples of the first jaw member.

A second handle is operably coupled to the housing and is selectively moveable relative to the first handle to actuate the first and second jaw members between a first position wherein the first and second jaw members of the end effector assembly are disposed in a spaced apart configuration relative to one another and second position wherein the jaw members cooperate to grasp tissue disposed therebetween. A first switch is disposed on the housing and is activatable to supply electrical energy from an electrical energy source to at least one of the electrically conductive plates of the first or second jaw members. A second switch is disposed on an inner facing surface of the first handle in alignment with the second handle such that actuation of the second handle activates the second switch during movement thereof. The second switch is operably connected to both electrically conductive plates of the first and second jaw members and is configured to supply electrical energy from an electrical energy source to tissue disposed between the electrically conductive plates to form a tissue seal.

A stapler mode activation mechanism is operably coupled to the second handle and is actuatable between a first, unactuated position, wherein movement of the second handle towards the first handle moves the jaw members to the second position and a second, actuated, position wherein movement of the second handle towards the first handle moves the jaw members to the second position and drives the staples through tissue disposed between the jaw members. In aspects according to the present disclosure, actuation of the stapler mode activation switch deactivates the second switch.

In aspects according to the present disclosure, a release mechanism is disposed on the housing and is operably associated with the end effector. The release mechanism is actuatable to uncouple the end effector from a distal end of the elongated shaft. In other aspects according to the present disclosure, the release mechanism is actuatable to couple and uncouple the end effector from the distal end of the shaft. In still other aspects according to the present disclosure, the release mechanism cooperates with a coupler disposed within the elongated shaft to uncouple the end effector from the shaft.

BRIEF DESCRIPTION OF THE DRAWINGS

Various aspects and features of the present disclosure are described herein with reference to the drawings, wherein like reference numerals identify similar or identical components, and wherein.

DETAILED DESCRIPTION

Figure 1:
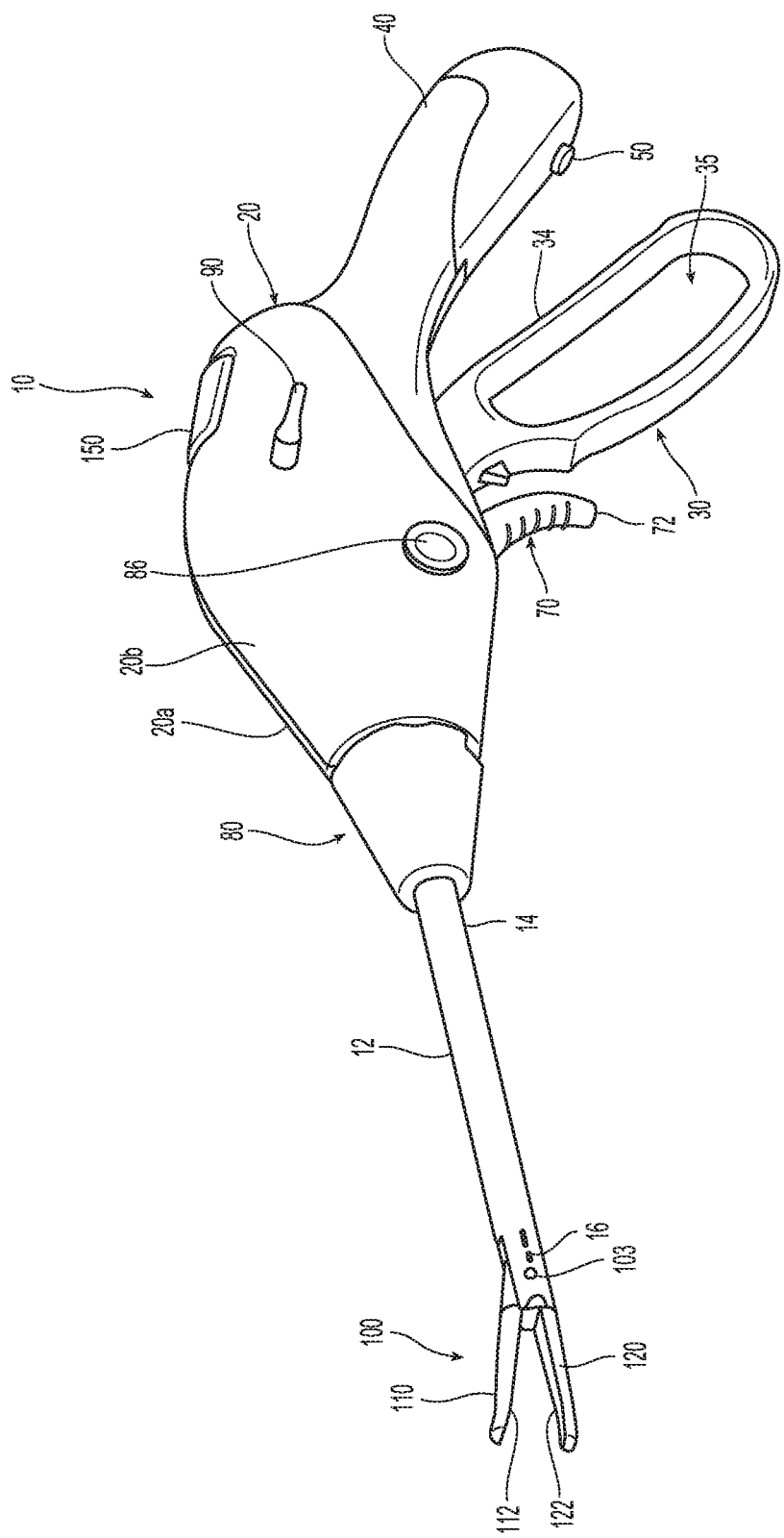
FIG. 1 is a perspective view of a surgical instrument in accordance with the present disclosure having two opposing jaw members at a distal end thereof.

Turning to FIG. 1, a surgical instrument 10 configured for use in accordance with the present disclosure is shown generally including a housing 20 that supports various actuators and switches, e.g., a movable handle 30, a trigger assembly 70, a rotation knob 80, a bipolar pre-coagulation activation switch 150, a suction irrigation lever 90, a coagulation activation switch 86 and a vessel sealing activation switch 50. Although illustrated and described herein as an electrosurgical forceps configured for use in laparoscopic or endoscopic surgical procedures, the aspects and features of the present disclosure are equally applicable for use with other surgical instruments configured for use in traditional open surgical procedures and/or laparoscopic or endoscopic surgical procedures. For the purposes herein, instrument 10 is generally described.

Housing 20 of instrument 10 is constructed of a first housing half 20a and a second housing half 20b that are configured to support an elongated shaft 12 at a proximal end 14 thereof. Housing halves 20a, 20b may be constructed of sturdy plastic, or other suitable material, and may be joined to one another by adhesives, ultrasonic welding, or other suitable assembly process. Housing 20 supports a stationary handle 40, movable handle 30, trigger assembly 70, and rotation knob 80. Movable handle 30, as detailed below, is operable to move a pair of opposing jaw members 110 and 120 of an end effector assembly 100 disposed at a distal end 16 of elongated shaft 12. Jaw members 110 and 120 are selectively movable via handle 30 between an open configuration (FIG. 1), wherein jaw members 110, 120 are disposed in spaced relation relative to one another, and a closed configuration (not shown), wherein jaw members 110, 120 are approximated relative to one another.

More specifically, compression of movable handle 30 towards stationary handle 40 serves to move a drive assembly (not shown) which, in turn, moves the jaw members 110, 120 of the end effector assembly 100 to the closed configuration and return of movable handle 30 away from stationary handle 40 serves to move the jaw members 110, 120 of the end effector assembly 100 back to the open configuration. Trigger assembly 70 is operable to extend and retract a knife blade 85 (see FIG. 4) between jaw members 110, 120 when the end effector assembly 100 is in the closed configuration. Rotation knob 80 serves to rotate elongated shaft 12 and end effector assembly 100 relative to housing 20.

Each jaw member 110, 120 includes an electrically conductive plate 112, 122, respectively, disposed thereon that is configured to conduct electrical energy to tissue when held therebetween. One or both electrically conductive plates, e.g., electrically conductive plate 122, includes a knife channel, e.g., knife channel 115, defined therein that is configured to allow selective reciprocation of the knife blade 85 therein upon actuation (e.g., squeezing) of a trigger 72 of trigger assembly 70.

To electrically control the jaw members 110, 120 and the various energy modalities associated therewith, housing 20 supports a variety of switches that provide different energy modalities to different electrodes disposed on the jaw members 110, 120. More particularly, switch 150 is disposed towards the proximal portion of housing 20 and is configured to provide bipolar energy to electrically conductive plates 112, 122 to pre-coagulate tissue prior to further tissue treatment by one of the other modalities as explained below. Activation of switch 150 provides a first energy polarity from a generator (not shown) to electrically conductive plate 112 and a second energy polarity to electrically conductive plate 122 such that electrical current passes through tissue when disposed between jaw members 110, 120. Pre-coagulating tissue and slowly closing (e.g., "slow close") the jaw members 110, 120 effectively pre-heats the tissue to facilitate further treatment. More particularly, the jaw members 110, 120 are slowly closed while activating the forceps 10. The speed of the jaw closure is closely regulated by the surgeon to maintain a blanched are of parenchyma around the jaw members 110, 120. Once completely closed the forceps is again activated to complete a seal. As a result of this technique liver parenchyma is crushed between the jaw members 110, 120 with sufficient coagulation and the liver can be divided with minimal bleeding from the liver parenchyma.

Slow close pre-coagulation allows the user to apply energy to tissue before the jaw members 110, 120 are completely closed. This is helpful in solid organ surgery, and potentially large tissue bundles, as the tissue between the jaw members 110, 120 may heat up enough to coagulate small vessels and parenchyma. Therefore, as the surgeon continues to move the jaw members 110, 120 into the closed position, there will be reduced bleeding. This may eliminate the need to address any potential "oozing" that may occur as well as create a cleaner operating field for better visualization.

Switch 86 is disposed on one or both sides 20a, 20b of housing 20 and is configured to supply energy to the distal tip 127, 227 of jaw member 120 depending on the configuration of the instrument 10, e.g., jaw member 120 may include a bipolar tip option (FIG. 3A) or a monopolar tip option (FIG. 3B) which is each activated via switch 86. More particularly and as best illustrated by FIG. 3A, the distal tip 127 of jaw member 120 may include a pair of electrodes 127a and 127b that cooperate to supply bipolar energy to tissue disposed proximate tip 127. Electrode 127a may be connected to an energy source (not shown) that supplies a first energy polarity to electrode 127a and electrode 127b may be connected to the energy source to supply a second energy polarity to electrode 127b such that an electrical current flows through tissue disposed therebetween. The energy source may be the same or a different energy source that energizes electrically conductive plates 112, 122.

An irrigation/suction port 128 is defined between the electrodes 127a, 127b (or proximate the electrodes 127a, 127b) to supply saline (or any other conductive medium) to the area proximate tip 127 to aid coagulation or enhance the coagulation effect. When used as an irrigation/suction port, fluids may be safely evacuated to improve visualization and assist in controlling the buildup of heat. As explained in more detail below, lever 90 on housing 20 is configured to control the delivery of fluid, e.g., saline, or the release of suction to port 128.

Figure 3B:
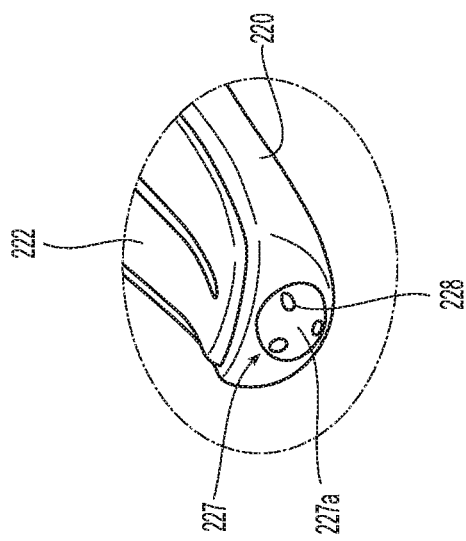
FIG. 3B is an enlarged, end view of the distal tip of one of the jaw members having a monopolar electrode integrated therewith.
Figure 3A:
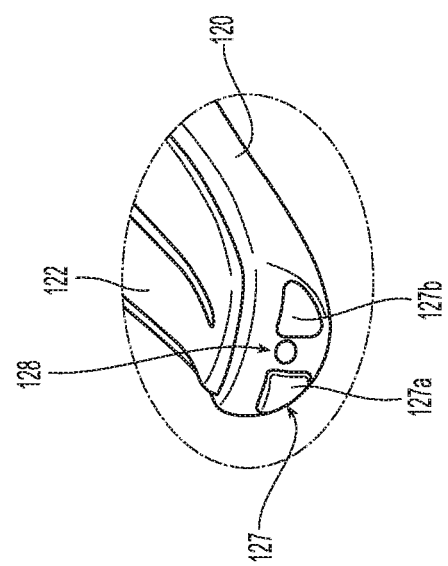
FIG. 3A is an enlarged, end view of a distal tip of one of the jaw members having a pair of bipolar electrodes integrated therewith.

As best illustrated by FIG. 3B, jaw member 120 may include a distal tip 227 that includes a monopolar electrode 227*a* that is energizable via switch 86 to provide monopolar energy to tissue proximate the distal tip 227. Electrode 227*a* may be ball-shaped and may be connected to an energy source (not shown) that supplies a first energy polarity to electrode 227*a* and a return electrode, e.g., a return pad (not shown), may be connected to the energy source to supply a second energy polarity to the return electrode such that an electrical current flows through tissue proximate the distal tip 227. Energy is concentrated at the tip electrode 227*a* and is generally dispersed at the return pad electrode due to the size differential between the two electrodes. An irrigation port or ports 228 may be disposed proximate electrode 227*a* to supply saline (or any other conductive medium) to the area proximate tip 227 to aid coagulation. Again, lever 90 on housing 20 is configured to control the delivery of fluid, e.g., saline, or the release of suction to port(s) 228.

Figure 2B:
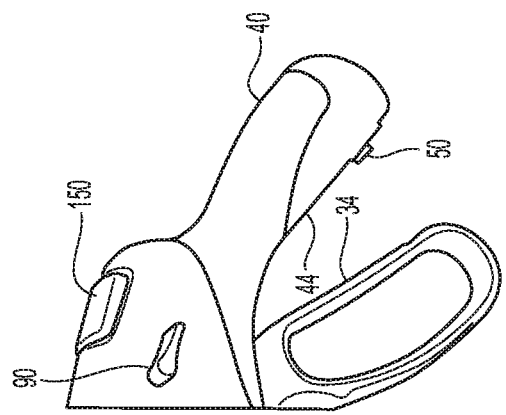
FIG. 2B is a rear perspective view of the surgical instrument of FIG. 1 showing the slow close bipolar switch and a vessel sealing, in-line activation switch.
Figure 2A:
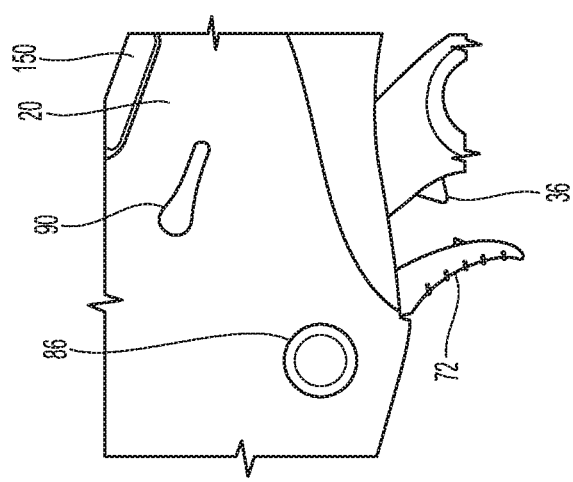
FIG. 2A is an enlarged, side view of a housing of the surgical instrument showing a suction irrigation control lever, a coagulation switch and a slow close bipolar switch.

Referring to FIGS. 2A and 2B and as mentioned above, lever 90 is disposed on one or both sides of housing 20 and is operable to supply fluid or suction to the operative site. Although the irrigation/suction ports 128, 228 are disposed on the distal tips 127, 227 of instrument 10, one or more ports may be disposed at different locations on the end effector assembly 100. Lever 90 is selectively movable from a neutral position (i.e., a position where neither irrigation or suction is supplied) to a first position where irrigation is supplied to one or more ports, e.g., port 128, or a second position where suction is supplied to one or more ports, e.g., port 128. For example and as shown in FIG. 2A, a user can actuate lever 90 in a first direction (upwardly) to initiate the flow of fluid to one or more ports, e.g., port 128, and a user can actuate lever 90 in a second direction (downwardly) to initiate the flow of suction to one or more ports, e.g., port 128. The user can toggle between positions as needed during a surgical procedure.

FIG. 2B shows activation switch 50 that is configured to provide electrosurgical energy to the end effector assembly 100 for sealing tissue when activated. Switch 50 is positioned as an in-line activation switch that is only activatable when the jaw members 110, 120 are closed about tissue. More particularly, switch 50 is disposed on a distal portion 44 of handle 40 angular registration with a proximal portion 34 of movable handle 30 such that during the range of motion from an open position (corresponding to the jaw members 110, 120 being disposed in a spaced apart position) to a closed position (corresponding to the jaw members 110, 120 being disposed in an approximated position) the proximal portion 34 of movable handle 30 activates the switch 50. A tactile sensation or audible tone (or both) may be operably associated with movable handle 30 or the switch 50 to advise the user prior to activation of energy. As mentioned above, upon activation, switch 50 is configured to supply electrosurgical energy to tissue disposed between electrically conductive plates 112, 122 of jaw members 110, 120, respectively, to effectively seal tissue. One or more algorithms associated with sealing technology may be employed to accomplish this purpose, e.g., Medtronic's Ligasure® algorithm, used with its proprietary vessel sealing generators, e.g., Force Triad™, Force FX™, Force EZ™ etc. and line of vessel sealing instruments, e.g., Ligasure Atlas™, Ligasure Precise™, Ligasure Impact™, Ligasure Advance™, Ligasure Maryland™, Ligasure Dolphin Tip, Ligasure Exact, etc.

Figure 4:
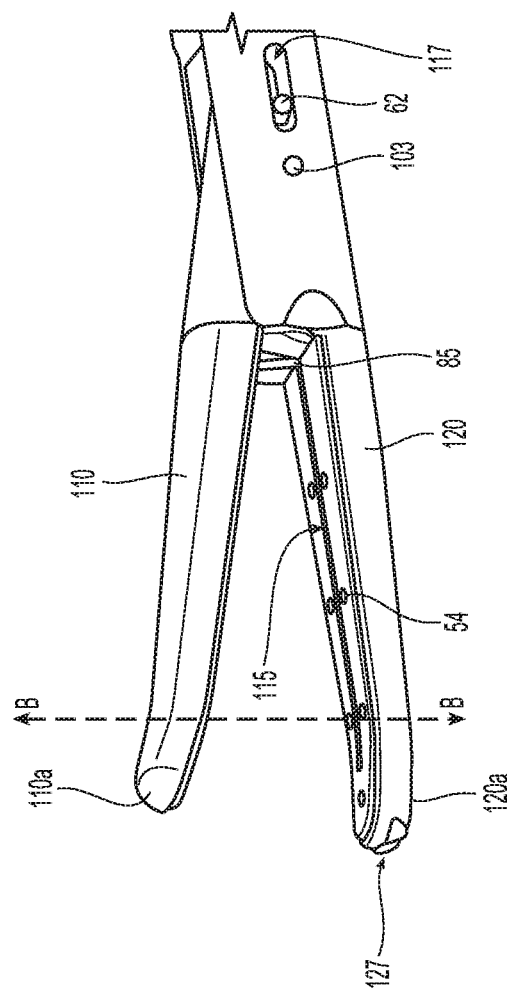
FIG. 4 is an enlarged, side view of the pair of jaw members disposed in an open position illustrating the curvature of the distal tip of the jaw members.

Referring to FIG. 4, as mentioned above, end effector assembly 100 includes jaw members 110, 120 each having an electrically conductive plate 112, 122 disposed thereon which cooperates to engage and treat tissue when one or more switches are activated, e.g., switch 150 and/or switch 50. The distal-most end of each jaw member 110, 120 includes a tip portion 110*a* and 120*a*, respectively, that are each configured to curve in the same direction (coplanar) along a transverse axis "B-B" defined through the jaw members 110, 120. The curved tip portions 110*a*, 120*a* are designed to aid visualization of tissue during use, e.g., aid visualizing tissue when plunging the tip portions 110*a*, 120*a* into parenchyma tissue. The tip portions 110*a*, 120*a* are also designed to help the surgeon visualize the location of the tips 110*a*, 120*a* when plunging the tips 110*a*, 120*a* into parenchyma. The jaw members 110, 120 may also be configured to close in a generally parallel fashion which optimizes the jaw members 110, 120 for transection parenchyma while leaving larger vessels and structures undamaged.

Jaw members 110, 120 are pivoted about a pivot pin 103 and relative to the distal end 16 of elongated shaft 12 between the open configuration (FIG. 4) and the closed configuration (not shown). In the closed configuration of end effector assembly 100, electrically-conductive plates 112, 122 of respective jaw members 110, 120 provide a clamping pressure to the tissue grasped therebetween. Also, in the closed configuration, a gap distance may be maintained between electrically-conductive plates 112, 122 by one or more stop members 54 disposed on either or both electrically-conductive plates 112, 122. The gap distance may be in the range of about 0.001 inches to about 0.010 inches or higher.

A drive assembly (not shown) operably couples movable handle 30 with end effector assembly 100 such that, as noted above, movable handle 30 is operable to move jaw members 110, 120 of end effector assembly 100 between the open configuration and the closed configuration. The drive assembly may include a drive rod slidably disposed within elongated shaft 12 and operably coupled to jaw members 110, 120, e.g., via a pin 62 associated therewith and extending through oppositely-angled slots, e.g., slot 117, defined within the proximal flanges of the jaw members, e.g., jaw member 110, such that proximal sliding of drive rod and pin 62 through elongated shaft 12 moves end effector assembly 100 from the open configuration to the closed configuration. However, the opposite configuration is also contemplated, as are other mechanisms for operably coupling the drive rod with jaw members 110, 120. The drive rod and pin 62 arrangement along with the drive assembly may be optimized to allow precise surgical feel and control of the movement of the jaw members 110, 120 during specific surgical procedures, e.g., clamp-crushing, to assist in identifying internal hepatic structures.

Movable handle 30 is pivotably coupled within housing 20 via a pivot pin (not shown) and is operably coupled to the drive rod such that movable handle 30 may be manipulated to impart longitudinal motion to drive rod and pin 62. As noted above, longitudinal movement of drive rod, in turn, moves end effector assembly 100 between the open and closed configurations. During initial movement of the movable handle 30, jaw members 110, 120 meet minimal resistance as they move towards the closed condition due to an internal spring maintaining a pre-compressed condition.

Once jaw members 110, 120 are closed about tissue and/or when jaw members 110, 120 otherwise meet sufficient resistance, further pivoting of movable handle 30 towards stationary handle 40 compresses the spring which essentially acts as a force-regulator to ensure that an appropriate clamping pressure is applied to tissue grasped between jaw members 110, 120. For tissue sealing, for example, this pressure may be within the range of about 3 kg/cm$^2$ to about 16 kg/cm$^2$; however, other suitable pressures may also be provided.

As noted above, the compression of spring enables the regulation of the clamping pressure applied to tissue grasped between jaw members 110, 120, allows the surgeon to regulate the jaw members 110, 120 during specific surgical procedures such as clamp crushing parenchyma, and enhances a surgeons "feel" when interacting with internal hepatic structures.

Referring to FIGS. 1 and 4, trigger assembly 70 may be manipulated to impart longitudinal motion to knife blade 85 (FIG. 4) to advance the knife blade 85 through knife channel(s) 115 defined within one or both of the jaw members 110, 120 (see FIG. 4). Trigger assembly 70 includes trigger 72 that is pivotally supported in housing 20 via a pivot pin (not shown) and is operably coupled to the knife blade 85. A spring (not shown) may be included that is configured to bias the knife blade 85 towards a retracted or proximal-most position, wherein knife blade 85 is positioned proximally of jaw members 110, 120, and trigger 72 is disposed in an un-actuated position. Upon actuation of trigger 72, e.g., upon pivoting of trigger 72 towards movable handle 30, knife blade 85 is advanced distally between jaw members 110, 120 to cut tissue grasped therebetween.

By combining the various electrical modalities and algorithms associated with the above identified switches 150, 86 and 50 along with the placement of various electrodes, e.g., 127, 227, or electrically conductive surfaces, e.g., 112, 122, on the end effector assembly 100, along with the unique shape of the distal ends 110a, 120a of the jaw members 110, 120, and the precise control of the movement of the jaw members 110, 120, a surgeon can utilize one instrument 10 for various types of hepatic surgeries, e.g., transection of liver parenchyma.

Figure 5A:
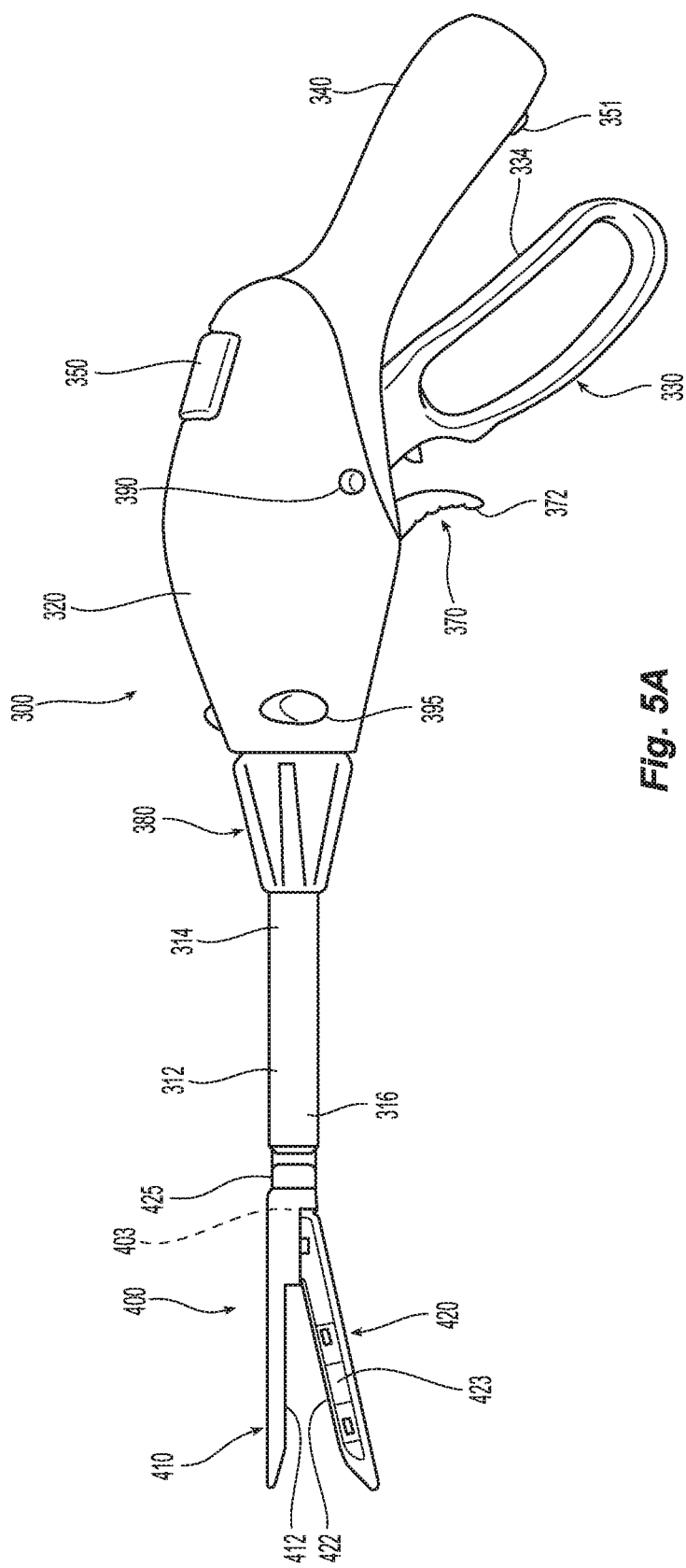
FIG. 5A is a side view of another embodiment of a surgical instrument according to the present disclosure shown with a replaceable staple cartridge, a bipolar activation switch, a vessel sealing, in-line activation switch, a stapler mode activation switch and a release mechanism.
Figure 5C:
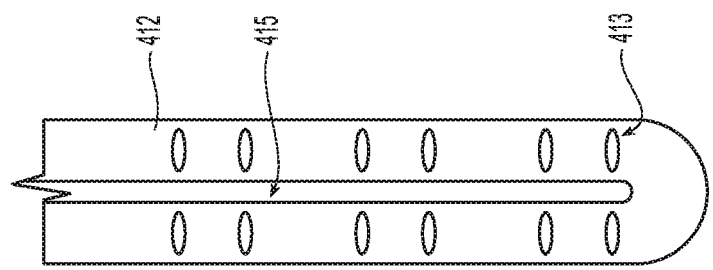
FIG. 5C is a top view of the other jaw member having a series of staple pockets defined therein in registration with the corresponding series of staples.
Figure 5B:
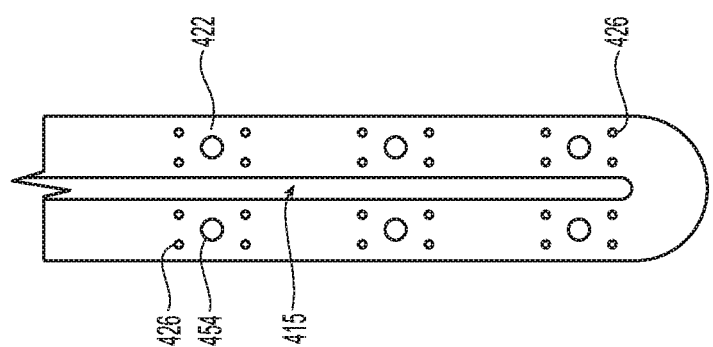
FIG. 5B is a top view of one of the jaw members having a series of staples disposed therein and a series of stop members disposed thereon.

FIG. 5 shows another embodiment of a surgical instrument for use with various types of surgeries, e.g., hepatic surgeries and is identified as reference number 300. Surgical instrument 300 includes a housing 320 that supports various actuators and switches, e.g., a movable handle 330, a trigger assembly 370, a rotation knob 380, a bipolar pre-coagulation activation switch 350, a staple cartridge release mechanism 395, a stapler mode activation switch 390 and a vessel sealing activation switch 351. An end effector 400 is attached to a distal end 316 of shaft 312 and includes a series of staples 426 therein configured for securing tissue.

Although illustrated and described herein as an electrosurgical instrument configured for use in laparoscopic or endoscopic surgical procedures, the aspects and features of the present embodiment are equally applicable for use with other surgical instruments configured for use in traditional open surgical procedures. For the purposes herein, instrument 300 is generally described. For the purposes of brevity, some of the features described with respect to instrument 10 are equally applicable to instrument 300.

Housing 320 of instrument 300 supports a stationary handle 340, movable handle 330, trigger assembly 370, and rotation knob 380. Movable handle 330, as detailed below, is operable to move a pair of opposing jaw members 410 and 420 of an end effector assembly 400 disposed at a distal end 316 of elongated shaft 312 and actuate the stapling function if the stapler mode activation switch 390 is actuated as explained in more detail below. Jaw members 410, 420 are selectively movable via handle 330 between an open configuration (FIG. 5), wherein jaw members 410, 420 are disposed in spaced relation relative to one another, and a closed configuration (not shown), wherein jaw members 410, 420 are approximated relative to one another.

End effector 400 is selectively coupleable to the distal end 316 of shaft 312 by a coupling 425. End effector 400 may be selectively replaced (once the staples 426 have fired) by actuating release mechanism 395. More particularly, actuation of release mechanism 395 uncouples the end effector 400 from the distal end 316 of the shaft 312 such that the used end effector 400 may be discarded and a new end effector 400 may be coupled to the distal end 316 of the shaft 312 in its place. Release mechanism 395 may be configured to simple uncouple the end effector 400 upon actuation thereof or may be configured to both couple and uncouple the end effector 400 upon actuation thereof. If only used for uncoupling, the distal end 316 of shaft 312 and the coupling 425 may be configured to automatically couple the end effector 400 and the distal end 316 of shaft 312 upon engagement, e.g., press-fit coupling, snap-fit coupling etc.

Similar to the embodiment shown with respect to FIG. 1, when the stapler mode activation switch 390 is unactuated (or disposed in an at rest configuration) compression of movable handle 330 towards stationary handle 340 serves to move a drive assembly (not shown) which, in turn, moves the end effector assembly 400 to the closed configuration and return of movable handle 330 away from stationary handle 340 serves to move end effector assembly 400 back to the open configuration. When stapler mode activation switch 390 is actuated, compression of handle 330 towards handle 340 not only moves the jaw members 410 and 420 relative to one another but also deploys the series of staples 426 (FIG. 5B) from a staple cartridge 423 disposed within jaw member 420 through tissue disposed between jaw members 410, 420 and against the seal plate 412 to deform the staples 426 once each staple 426 successfully pierces the tissue. A corresponding series of pockets 413 may be defined in seal plate 412 to facilitate deformation of each staple 426.

The jaw members 410, 420 are configured to include respective electrically conductive sealing plates 412, 422, to allow the sealing plates 412, 422 to electrically treat tissue disposed therebetween (as explained in more detail below with respect to activation switches 350 and 351). One or both electrically conductive plates, e.g., electrically conductive plate 422, includes a knife channel 415, defined therein that is configured to allow selective reciprocation of the knife blade, e.g., knife blade 85 discussed above, therein upon actuation (e.g., squeezing) of trigger 372.

The distal tips 427a, 427b of the jaw members 410, 420 are configured to facilitate plunging the jaw members 410, 420 into the liver parenchyma and to enhance the overall "feel" of internal hepatic structures. The distal ends of the jaw members 410, 420 are also configured to avoid damaging internal tissue structures. The jaw members 410, 420 may be coated with a hexamethyldisiloxane (HMDSO) coating to facilitate cleaning the jaw members 410, 420 during or after use.

Trigger 372 of trigger assembly 370 is operable to extend and retract a knife blade 85 (see FIG. 4) between jaw members 410, 420 when the end effector assembly 400 is in the closed configuration. Rotation knob 380 serves to rotate elongated shaft 312 and end effector assembly 400 relative to housing 320.

Similar to above, to electrically control the jaw members 410, 420 and the various energy modalities associated therewith, housing 320 supports a variety of switches that provide different energy modalities to different electrodes disposed on the jaw members 410, 420. More particularly, switch 350 is disposed towards the proximal portion of housing 320 and is configured to provide bipolar energy to electrically conductive plates 412, 422 to pre-coagulate tissue prior to further tissue treatment by one of the other modalities or deployment of staples 426 as explained below. Activation of switch 350 provides a first energy polarity from a generator (not shown) to electrically conductive plate 412 and a second energy polarity to electrically conductive plate 422 such that electrical current passes through tissue when disposed between jaw members 410, 420. Pre-coagulating tissue effectively pre-heats the tissue to facilitate further treatment.

Switch 351 is disposed on a distal facing side of handle 340 and is configured to provide electrosurgical energy to the end effector assembly 400 for sealing tissue when activated. Switch 351 is positioned as an in-line activation switch that is only activatable when the jaw members 410, 420 are closed about tissue. More particularly, switch 351 is disposed in angular registration with a proximal portion 334 of movable handle 330 such that during the range of motion from an open position (corresponding to the jaw members 410, 420 being disposed in a spaced apart position) to a closed position (corresponding to the jaw members 410, 420 being disposed in an approximated position) the proximal portion 334 of movable handle 330 activates the switch 351. A tactile sensation or audible tone (or both) may be operably associated with movable handle 330 or the switch 351 to advise the user prior to activation of energy.

As mentioned above, upon activation, switch 351 is configured to supply electrosurgical energy to tissue disposed between electrically conductive plates 412 and 422 of jaw members 410 and 420, respectively, to effectively seal tissue. One or more algorithms associated with sealing technology may be employed to accomplish this purpose, e.g., Covidien's Ligasure® algorithm, used with its proprietary vessel sealing generators, e.g., Force Triad™, Force FX™, Force EZ™, etc. and line of vessel sealing instruments, e.g., Ligasure Atlas™, Ligasure Precise™, Ligasure Impact™, Ligasure Advance™, Ligasure Maryland™ Ligasure Dolphin Tip, Ligasure Exact, etc.

Jaw members 410, 420 are pivoted about a pivot pin 403 and relative to the distal end 316 of elongated shaft 312 between the open configuration and the closed configuration (not shown). In the closed configuration of end effector assembly 400, electrically-conductive plates 412, 422 of respective jaw members 410, 420 provide a clamping pressure to the tissue grasped therebetween. Also, in the closed configuration, a gap distance may be maintained between electrically-conductive plates 412, 422 by one or more stop members 454 (FIG. 5B) disposed on either or both electrically-conductive plates 412, 422. The gap distance may be in the range of about 0.001 inches to about 0.006 inches or higher.

A drive assembly (not shown) operably couples movable handle 330 with end effector assembly 400 such that, as noted above, movable handle 330 is operable to move jaw members 410, 420 of end effector assembly 400 between the open configuration and the closed configuration. The drive assembly may include a drive rod (not shown) slidably disposed within elongated shaft 312 and operably coupled to jaw members 410, 420, e.g., via a pin, e.g., pin 62 of FIG. 4) associated therewith and extending through oppositely-angled slots (not shown) defined within the proximal flanges of the jaw members such that proximal sliding of drive rod and pin 62 through elongated shaft 312 moves end effector assembly 400 from the open configuration to the closed configuration. The drive rod and pin 62 arrangement along with the drive assembly may be optimized to allow precise surgical feel and control of the movement of the jaw members 410, 420 during specific surgical procedures, e.g., clamp-crushing parenchyma, to assist in identifying "feeling" internal hepatic structures.

Movable handle 330 is pivotably coupled within housing 320 via a pivot pin (not shown) and is operably coupled to the drive rod such that movable handle 330 may be manipulated to impart longitudinal motion to drive rod and pin 62 (See FIG. 4). As noted above, longitudinal movement of drive rod, in turn, moves end effector assembly 400 between the open and closed configurations. During initial movement of the movable handle 330, jaw members 410, 420 meet minimal resistance as they move towards the closed condition due to an internal spring maintaining a pre-compressed condition.

Once jaw members 410, 420 are closed about tissue and/or when jaw members 410, 420 otherwise meet sufficient resistance, further pivoting of movable handle 330 towards stationary handle 340 compresses the spring which essentially acts as a force-regulator to ensure that an appropriate clamping pressure is applied to tissue grasped between jaw members 410, 420. For tissue sealing, for example, this pressure may be within the range of about 3 kg/cm$^2$ to about 16 kg/cm$^2$; however, other suitable pressures may also be provided.

As noted above, the compression of spring enables both the regulation of the clamping pressure applied to tissue grasped between jaw members 410, 420, allows the surgeon to regulate the jaw members 410, 420 during specific surgical procedures such as clamp crushing parenchyma, and enhances a surgeons "feel" when interacting with internal hepatic structures.

Trigger 372 of trigger assembly 370 may be manipulated to impart longitudinal motion to knife blade, e.g., knife blade 85 (FIG. 4), to advance the knife blade through knife channel(s) 415, defined within one or both of the jaw members 110, 120. Trigger 372 that is pivotally supported in housing 320 via a pivot pin (not shown) and is operably coupled to the knife blade. A spring (not shown) may be included that is configured to bias the knife blade towards a retracted or proximal-most position, wherein knife blade is positioned proximally of jaw members 410, 420, and trigger 372 is disposed in an un-actuated position. Upon actuation of trigger 372, e.g., upon pivoting of trigger 372 towards movable handle 330, the knife blade is advanced distally between jaw members 410, 420 to cut tissue grasped therebetween.

In use, a surgeon approximates tissue by compressing the handle 330 towards handle 340 to move the jaw members 410, 420 toward one another about tissue. Once approximated, the surgeon has the option of treating the tissue with electrical energy (coagulating tissue) by activating activation switch 350 and sealing tissue by activating switch 351. For example, the surgeon can plunge the tips of the jaw members 410, 420 into the liver parenchyma and feel for various hepatic structures. If desired, the surgeon can clamp crush the tissue and activate switch 350 to coagulate small vessels as the surgeon slowly closes the jaw members 410, 420 about tissue. Alternatively, if the surgeon wants to seal medium vessels or structures, the surgeon can approximate the tissue between the jaw members 410, 420 and fully compress handle 330 against handle 340 to activate in-line activation switch 351 to energize tissue with a sealing algorithm (as explained above) to effectively seal tissue. The in-line activation switch 351 may include audible or tactile feedback to alert the surgeon prior to activation of electrical energy.

When a surgeon encounters larger tissue structures and pedicles, the surgeon may opt to staple the tissue. This may occur before, after or in lieu of treating the tissue with electrical energy to coagulate or seal the tissue. In order to staple the tissue, the surgeon opens the jaw members 410, 420 and orients the jaw members 410, 420 via rotating member 380 about the tissue structure. The surgeon then activates the stapler mode activation switch 390 which couples handle 330 to an internal stapler drive rod (not shown) disposed in housing 320 and shaft 312 which, upon actuation of handle 330 towards handle 340, drives a series of staples 426 from a staple cartridge 423 into and through the tissue. Upon release of handle 330, the internal stapler drive rod retracts to release the staples 426. Internal stapler drive rod may be configured to communicate with another drive rod (not shown) disposed in end effector 400 and connected through coupling 425.

The stapler mode activation switch 390 when activated may be configured to disconnect the vessel sealing activation switch 351 either mechanically or electrically. Alternatively, full compression of handle 330 against handle 340 may activate the vessel sealing activation mode and provide vessel sealing energy to the tissue depending upon a particular purpose.

Once sealed or stapled, the surgeon may activate the knife trigger 372 to actuate a knife, e.g., knife 85, through the tissue. Shaft 312 may be configured to include a knife drive rod (not shown) that communicates with another knife drive rod (not shown) disposed in end effector 400 and connected through coupling 425 to advance the knife when trigger 372 is actuated. Once stapled, the surgeon may actuate release switch 395 to release the end effector 400 and staple cartridge 423 for replacement. The instrument 300 (or instrument 10) may be disposable or include disposable features (e.g., reposable).

By combining the various electrical modalities and algorithms associated with the above identified switches 350 and 351 along with electrically conductive plates, e.g., 412, 422, on the end effector assembly 400, along with the unique shape of the distal ends of the jaw members 410, 420, and the precise control of the movement of the jaw members 410, 420, a surgeon can utilize one instrument 300 for various types of hepatic surgeries, e.g., transection and stapling of liver parenchyma.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical instrument, comprising:
   a housing having a first handle depending therefrom;
   an elongated shaft extending distally from the housing;
   an end effector disposed at a distal end of the elongated shaft, the end effector including first and second jaw members each having an electrically conductive plate disposed thereon, the respective electrically conductive plates of the first and second jaw members disposed in vertical opposition relative to one another, the first jaw member including a staple cartridge configured to house a series of staples therein;
   a second handle operably coupled to the housing and selectively moveable relative to the first handle to actuate the first and second jaw members between a first position wherein the first and second jaw members of the end effector assembly are disposed in a spaced apart configuration relative to one another and a second position wherein the jaw members cooperate to grasp tissue disposed therebetween;
   a first switch disposed on the housing and activatable to supply electrical energy from an electrical energy source to at least one of the electrically conductive plates of the first or second jaw members; and
   a stapler mode activation switch operably coupled to the second handle, the stapler mode activation switch actuatable between a first, unactuated position, wherein movement of the second handle towards the first handle moves the jaw members to the second position and a second, actuated, position wherein movement of the second handle towards the first handle moves the jaw members to the second position and drives the staples through tissue disposed between the jaw members.

2. The surgical instrument according to claim 1 wherein the second jaw member includes a corresponding series of pockets defined therein disposed in registration with the series of staples disposed in the first jaw member.

3. The surgical instrument according to claim 1 wherein the first switch, when activated, provides electrical energy to the respective at least one jaw member to coagulate tissue.

4. The surgical instrument according to claim 1 further comprising a second switch disposed on an inner facing surface of the first handle in alignment with the second handle such that actuation of the second handle activates the second switch during movement thereof, the second switch operably connected to both electrically conductive plates of the first and second jaw members and configured to supply electrical energy from an electrical energy source to tissue disposed between the electrically conductive plates.

5. The surgical instrument according to claim 4 wherein the second switch is configured to supply electrical energy to seal tissue disposed between the electrically conductive plates of the first and second jaw members.

6. The surgical instrument according to claim 5 wherein at least one of the jaw members includes at least one stop member disposed thereon configured to regulate a gap between electrically conductive plates when the jaw members are disposed in the second position.

7. The surgical instrument according to claim 4 wherein the second switch is configured to include tactile feedback or an audible tone to advise the user prior to activation of electrical energy.

8. The surgical instrument according to claim 1, further comprising:
a trigger assembly operably associated with the housing, the trigger assembly including a trigger configured to selectively advance a knife between the first and second jaw members upon actuation thereof.

9. The surgical instrument according to claim 8 wherein the knife is advanceable via actuation of the trigger between a first position wherein the knife is disposed proximal the first and second electrically conductive plates of the first and second jaw members to a second position wherein the knife translates through respective channels defined within the first and second electrically conductive plates of the first and second jaw members.

10. The surgical instrument according to claim 1 further comprising a rotation knob operably associated with the elongated shaft of the housing, the rotation knob selectively rotatable relative to the housing to rotate the elongated shaft and the end effector at the distal end thereof.

11. The surgical instrument according to claim 1 further comprising a release mechanism disposed on the housing and operably associated with the end effector, the release mechanism actuatable to uncouple the end effector from a distal end of the elongated shaft.

12. The surgical instrument according to claim 11 wherein the release mechanism is actuatable to couple and uncouple the end effector from the distal end of the shaft.

13. The surgical instrument according to claim 11 wherein the release mechanism cooperates with a coupler disposed within the elongated shaft to uncouple the end effector from the shaft.

14. A surgical instrument, comprising:
a housing having a first handle depending therefrom;
an elongated shaft extending distally from the housing;
an end effector disposed at a distal end of the elongated shaft, the end effector including first and second jaw members each having an electrically conductive plate disposed thereon, the first jaw member including a staple cartridge configured to house a series of staples therein and the second jaw member including a series of corresponding pockets defined therein in vertical registration with the series of staples of the first jaw member;
a second handle operably coupled to the housing and selectively moveable relative to the first handle to actuate the first and second jaw members between a first position wherein the first and second jaw members of the end effector assembly are disposed in a spaced apart configuration relative to one another and a second position wherein the jaw members cooperate to grasp tissue disposed therebetween;
a first switch disposed on the housing and activatable to supply electrical energy from an electrical energy source to at least one of the electrically conductive plates of the first or second jaw members;
a second switch disposed on an inner facing surface of the first handle in alignment with the second handle such that actuation of the second handle activates the second switch during movement thereof, the second switch operably connected to both electrically conductive plates of the first and second jaw members and configured to supply electrical energy from an electrical energy source to tissue disposed between the electrically conductive plates to form a tissue seal; and
a stapler mode activation switch operably coupled to the second handle, the stapler mode activation switch actuatable between a first, unactuated position, wherein movement of the second handle towards the first handle moves the jaw members to the second position and a second, actuated, position wherein movement of the second handle towards the first handle moves the jaw members to the second position and drives the staples through tissue disposed between the jaw members.

15. The surgical instrument according to claim 14 wherein actuation of the stapler mode activation switch deactivates the second switch.

16. The surgical instrument according to claim 14 further comprising a release mechanism disposed on the housing and operably associated with the end effector, the release mechanism actuatable to uncouple the end effector from a distal end of the elongated shaft.

17. The surgical instrument according to claim 16 wherein the release mechanism is actuatable to couple and uncouple the end effector from the distal end of the shaft.

18. The surgical instrument according to claim 16 wherein the release mechanism cooperates with a coupler disposed within the elongated shaft to uncouple the end effector from the shaft.

19. A surgical instrument, comprising:
a housing having a first handle;
an elongated shaft extending distally from the housing;
an end effector disposed at a distal end of the elongated shaft, the end effector including first and second jaw members each having an electrically conductive plate disposed in vertical opposition relative to one another, the first jaw member including a staple cartridge configured to house a series of staples within the staple cartridge;
a second handle operably coupled to the housing and selectively moveable relative to the first handle to actuate the first and second jaw members between a first position wherein the first and second jaw members of the end effector assembly are disposed in a spaced apart configuration relative to one another and a second position wherein the jaw members cooperate to grasp tissue disposed between the jaw members;

a first switch operably coupled to at least one of the electrically conductive plates of the first or second jaw members and activatable to supply electrical energy from an electrical energy source; and a stapler mode activation switch operably coupled to the second handle, the stapler mode activation switch actuatable between a first, unactuated position, wherein movement of the second handle towards the first handle moves the jaw members to the second position and a second, actuated, position wherein movement of the second handle towards the first handle moves the jaw members to the second position and drives the staples through tissue disposed between the jaw members.

20. The surgical instrument according to claim 19 further comprising a lever operably associated with the housing and configured to supply fluid or suction from a fluid or suction source to a port defined within at least one of the first or second jaw members.

* * * * *